US011274120B2

(12) United States Patent
Chialvo et al.

(10) Patent No.: US 11,274,120 B2
(45) Date of Patent: Mar. 15, 2022

(54) METHOD FOR COMPREHENSIVE EXTRACTION OF CYCLOPEPTIDE TOXINS AND OTHER METABOLITES

(71) Applicant: The Board of Trustees of The University of Alabama, Tusclaoosa, AL (US)

(72) Inventors: Clare Scott Chialvo, Banner Elk, NC (US); Lukasz Ciesla, Northport, AL (US)

(73) Assignee: The Board of Trustees of The University of Alabama, Tuscaloosa, AL (US)

( * ) Notice: Subject to any disclaimer, the term of this patent is extended or adjusted under 35 U.S.C. 154(b) by 0 days.

(21) Appl. No.: 16/905,090

(22) Filed: Jun. 18, 2020

(65) Prior Publication Data
US 2021/0054022 A1   Feb. 25, 2021

Related U.S. Application Data (60) Provisional application No. 62/888,804, filed on Aug. 19, 2019.

(51) Int. Cl.
*C07K 7/64* (2006.01)
*C07K 1/14* (2006.01)

(52) U.S. Cl.
CPC .................... *C07K 1/145* (2013.01)

(58) Field of Classification Search
None
See application file for complete search history.

(56) References Cited

U.S. PATENT DOCUMENTS 6,669,972 B2 * 12/2003 Blortz ............... A23L 27/24
426/52

OTHER PUBLICATIONS

Zhang et al. Techniques forextraction and isolation of natural products: a comprehensive review, Chin Med (2018) 13:20, 1-26 (Year: 2018).*
Berger, K.J., Guss, D.A., 2005. Mycotoxins revisited: Part I. The Journal of emergency medicine 28, 53-62.
Beutler, J.A., Der Marderosian, A.H., 1981. Chemical variation in Amanita. Journal of Natural Products 44, 422-431.
Diaz, J.H., 2005. Syndromic diagnosis and management of confirmed mushroom poisonings. Critical Care Medicine 33, 427-436.
Enjalbert, F., Gallion, C., Jehl, F., Monteil, H., 1993. Toxin content, phallotoxin and amatoxin composition of Amanita phalloides tissues. Toxicon: official journal of the International Society on Toxinology 31, 803-807.
Enjalbert, F., Gallion, C., Jehl, F., Monteil, H., Faulstich, H., 1992. Simultaneous assay for amatoxins and phallotoxins in Amanita phalloides Fr. by high-performance liquid chromatography. Journal of Chromatography 598, 227-236.
Faulstich, H., Brodner, O., Walch, S., Wieland, T., 1975. Components of green deathcap toadstool, Amanita phalloides, 49. Phallisacin and Phallacin, 2 newly detected phallotoxins, and some amides of phallacidin. Annalen Der Chemie-Justus Liebig 1975, 2324-2330. English Abstract included in text.
Giddings, J. Calvin, et al. High pressure gas chromatography of nonvolatile species. Science 162.3849 (1968): 67-73.
Hallen, H.E., Watling, R., Adams, G.C., 2003. Taxonomy and toxicity of Conocybe lactea and related species. Mycological Research 107, 969-979.
Jaenike, J., 1985. Parasite pressure and the evolution of amanitin tolerance in *Drosophila*. Evolution 39, 1295-1301.
Jaenike, J., 1989. Genetic population structure of *Drosophila tripunctata*: Patterns of varitation and covariation of traits affecting resource use. Evolution 43, 1467-1482.
Jaenike, J., Grimaldi, D.A., Sluder, A.E., Greenleaf, A.L., 1983. α-Amanitin tolerance in mycophagous *Drosophila*. Science 221, 165-167.
Karlson-Stiber, C., Persson, H., 2003. Cytotoxic fungi—an overview. Toxicon: official journal of the International Society on Toxinology 42, 339-349.
Li, C., Oberlies, N.H., 2005. The most widely recognized mushroom: chemistry of the genus *Amanita*. Life sciences 78, 532-538.
Lindell, T.J., Weinberg, F., Morris, P.W., Roeder, R.G., Rutter, W.J., 1970. Specific inhibition of nuclera RNA polymerase II by α-amanitin. Science 170, 447-449.
Matinkhoo, Kaveh, et al. "Synthesis of the death-cap mushroom toxin α-amanitin." Journal of the American Chemical Society 140.21 (2018): 6513-6517.
Munekata, E., Faulstich, H., Wieland, T., 1978. Components of green deathcap toadstool Amanita phalloides, 55. peptide syntheses, 62. isolation, characterization and total synthesis of prophalloin (pro4-phalloin), a non-toxic probable precursor of phallotoxins. Justus Liebigs Annalen Der Chemie 1978, 776-784.
Scott Chialvo, C.H., Werner, T., 2018. *Drosophila*, destroying angels, and deathcaps! Oh my! A review of mycotoxin tolerance in the genus *Drosophila*. Frontiers in Biology 13, 91-102.
Spicer, G.S., Jaenike, J., 1996. Phylogenetic analysis of breeding site use and α-Amanitin tolerance within the *Drosophila quinaria* species group. Evolution 50, 2328-2337.

(Continued)

*Primary Examiner* — Thomas S Heard
(74) *Attorney, Agent, or Firm* — Meunier Carlin & Curfman LLC (57) ABSTRACT

Methods for extracting metabolites from mushroom comprising dispersing a sample of the mushroom; contacting the sample with a first solvent system at a temperature of 80° C. or greater to extract at least a first portion of metabolites from the sample; and contacting the sample with a second solvent system at a temperature of 80° C. or greater to extract at least a second portion of metabolites from the sample, wherein the combined first portion of metabolites and the second portion of metabolites include primary and secondary metabolites from the mushroom. A high-throughput process for establishing a metabolic profile of a mushroom, such as *Amanita* mushroom, can comprise extracting metabolites from mushroom and analyzing the extracted metabolites by automatic peak recognition or peak integration. Assay for identifying and/or assessing candidate metabolites extracted from *Amanita* mushroom are also disclosed.

12 Claims, 7 Drawing Sheets

(56) References Cited

OTHER PUBLICATIONS

Stump, A.D., Jablonski, S.E., Bouton, L., Wilder, J.A., 2011. Distribution and mechanism of alpha-amanitin tolerance in mycophagous *Drosophila* (Diptera: Drosophilidae). Environmental Entomology 40, 1604-1612.
Tang, Shanshan, et al. "Cyclopeptide toxins of lethal amanitas: compositions, distribution and phylogenetic implication." Toxicon 120 (2016): 78-88.
Wieland, T., 1968. Poisonous principles of mushrooms of the genus *Amanita*. Science 159, 946-952.
Wieland, T., 1983. The toxic peptides from Amanita mushrooms. International Journal of Peptide and Protein Research 22, 257-276.
Xue, Jing-Hua, et al. "Cyclopeptides from Amanita exitialis." Natural products and bioprospecting 1.1 (2011): 52-56.

* cited by examiner

METHOD FOR COMPREHENSIVE EXTRACTION OF CYCLOPEPTIDE TOXINS AND OTHER METABOLITES

CROSS REFERENCE TO RELATED APPLICATIONS

This application claims the benefit of priority to U.S. Provisional Application No. 62/888,804 filed Aug. 19, 2019, the disclosure of which is incorporated herein by reference in its entirety.

STATEMENT REGARDING FEDERALLY SPONSORED RESEARCH

This invention was made with Government Support under Grant No. DEB-1737869 awarded by the National Science Foundation. The Government has certain rights in the invention.

FIELD

The present disclosure generally relates to extraction methods, particularly for extraction of metabolites from mushrooms.

BACKGROUND

Natural products remain a rich source of biologically active compounds and many plant/fungal and bacterial metabolites are investigated for their pharmacological and toxicological effects. Interestingly, when investigating biological effects of a complex matrix, using animal feeding assays, most studies attribute the observed experimental effects to one compound or a set of known compounds and disregard the other secondary metabolites in the sample. Furthermore, secondary metabolite profiles vary from sample to sample and depend on many factors, such as collection site, drying and storing conditions or extraction method. Thus, the observed biological effect from such feeding assays can only be attributed to the specific sample used in the experiment.

*Amanita phalloides* mushrooms (Death Caps), for example, contain a mixture of cyclopeptide toxins that are the source of the mushroom's toxicity. Cyclopeptides are defined by the presence of a sulfur-linked tryptophan and unusual hydroxylated amino acids. There are three cyclopeptide subclasses (i.e., amatoxins, phallotoxins, and virotoxins) that differ based on chemical structure (bicyclic octapeptides, bicyclic heptapeptides, and monocyclic heptapeptides respectively). Of these subclasses, only amatoxins are readily absorbed through the digestive tract; thus, amatoxins, such as α-amanitin, are primarily responsible for fatalities attributed to cyclopeptides. Amatoxins act by binding to RNA polymerase II, which leads to cell death by inhibiting mRNA production. Within *A. phalloides*, 14 amatoxins and phallotoxins occur, and both the tissue type and life stage of the mushroom influence the concentration of these toxins. For example, Enjalbert et al. (Toxicon: official journal of the International Society on Toxinology, 1993, 31, 803-807) determined that α-amanitin constitutes 17% of the toxin load in the cap, but only 8.8% of the toxin load in the bulb.

While *A. phalloides* and other mushrooms that contain cyclopeptides are lethal to many eukaryotic organisms, 17 mushroom-feeding *Drosophila* species use these toxic mushrooms as developmental hosts along with other non-toxic *Basidiomycota* mushrooms. Little is known about cyclopeptide tolerance in these fly species, but their toxin tolerance is not due to mutations in RNA polymerase II that would prevent the toxin binding. Thus far, studies examining cyclopeptide tolerance in the mushroom-feeding *Drosophila* focused exclusively on α-amanitin. There is a need for methods to characterize toxin tolerance using feeding assays that more closely resemble the wild mushrooms. Also, as there are multiple reports describing the effects of co-extracted compounds on pharmacological activity of selected metabolites, there is a need to extract all toxins including secondary metabolites from toxic mushrooms that could interact synergistically or antagonistically with the toxins.

There are currently no standardized operational procedures describing the use of complex matrices in animal feeding assays exist. Additionally, the available extraction protocols for mushrooms were optimized to extract polar cyclopeptides, disregarding less polar metabolites including some phallotoxins present in the sample. In an ideal experimental setup, the model organism, mushroom-feeding *Drosophila*, should be reared in its natural habitat with unlimited access to freely-growing mushrooms. Additionally, the secondary metabolite profile of each mushroom used in the study should be strictly monitored, to correctly interpret the experimental outcomes. Since the implementation of this model may be complex, feeding assays using natural product extracts need to be developed. One of the greatest challenges associated with feeding assays using complex natural mixtures is the complexity of these samples. Further, the secondary metabolite profile of natural extracts varies from sample to sample and contributes greatly to the experimental outcome. In addition, the complexity and variability of natural products is one of the most commonly overlooked problems in designing experiments with animal feeding assays. Thus, the absence of any regulations when using extracts in animal feeding assays results in a lack of reproducibility of experiments involving the use of these complex natural mixtures. Furthermore, correct interpretation of experimental data is also jeopardized by the lack of detailed information related to extraction and secondary metabolite profile of the natural sample.

There is a need for an exhaustive extraction protocol for cyclopeptides and other secondary metabolite. There is also a need for recommendations of best practices when utilizing natural product extracts in feeding assays. There is a need to detail the conserved fragmentation pattern of cyclopeptides found in mushrooms. The compositions and methods disclosed herein address these and other needs.

SUMMARY

In accordance with the purposes of the disclosed methods, as embodied and broadly described herein, the disclosed subject matter relates to methods for extracting primary and secondary metabolites from a biological sample, such as fungi. In some embodiments, the primary and secondary metabolites include cyclopeptide toxins. The biological sample is preferably obtained from a mushroom. In certain embodiments, methods for extracting metabolites from mushrooms are disclosed.

The methods can include dispersing a sample of the mushroom; contacting the sample with a first solvent system in an extraction cell at a temperature of 80° C. or greater for a sufficient time to extract at least a first portion of metabolites from the sample; and contacting the sample with a second solvent system in an extraction cell at a temperature of 80° C. or greater for a sufficient time to extract at least a second portion of metabolites from the sample, wherein the combined first portion of metabolites and the second portion of metabolites include primary and secondary metabolites from the mushroom. The mushroom used in the methods disclosed herein can be selected from any mushroom containing cyclopeptide toxins, such as species occurring in *Amanita, Agaricus, Boletus, Lactarius, Lepiota, Russula, Tricholoma, Coprinus*, or *Pluteus* genus. In some examples, the mushroom can include a species selected from *Amanita tenuifolia, Amanita bisporigera, Amanita verna, Amanita virosa, Amanita phalloides, Amanita brunnescens, Amanita ocreata, Cantharellus* spp., *Cortinarius orellanus, Chlorophyllum molybdites, Coprinus atrimentarius, Coprinus comatus; Coprinus micaceus, Entoloma lividum, Galerina autumnalis, Leucoagaricus brunnea, Lepiota josserandii, Lepiota helveola, Lepiota subincarnata, Leucocoprinus rachodes, Leucocoprinus procera, Omphalotus olearius, Paxillus involutus, Tricholomopsis platyphylla, Tricholoma pardinum, Tricholoma virgatum, Tricholoma myomyces*, or a combination thereof.

The mushroom sample can be grounded prior to dispersing. Dispersing the sample of mushroom can comprise mixing a ground sample of mushroom with small particulates, such as sand.

The first solvent system used in extraction can be an aqueous solvent system. In some embodiments, the first solvent system can comprise water and a polar organic solvent. For example, the first solvent system can comprise water and an alcohol. Suitable alcohols can include methanol, ethanol, propanol such as isopropanol, or a mixture thereof. In some instances, the first solvent system can be an aqueous solvent system comprising water and a polar organic solvent (for e.g., water and methanol) in a volume ratio of from 1:5 to 5:1 or from 1:2 to 2:1.

The second solvent system can comprise an organic solvent, and in some cases, can be a non-aqueous solvent system. In some embodiments, the second solvent system can comprise a polar organic solvent, a non-polar organic solvent, or a mixture thereof. For example, the second solvent system can comprise an alcohol. Suitable alcohols can include methanol, ethanol, propanol such as isopropanol, or a mixture thereof. In some instances, the second solvent system consists essentially of an alcohol such as methanol.

The first solvent system and/or the second solvent system may further comprise up to 5% by weight of an additive such as buffer salts, acids, and/or bases.

Extraction of the first portion of metabolites and the second portion of metabolites from the sample can be carried out in any order and by means of an accelerated solvent extraction. For example, extraction of the first portion of metabolites and the second portion of metabolites from the sample can be carried out at a temperature from 80° C. to 160° C., such as from 85° C. to 150° C., or from 100° C. to 130° C. In some instances, the method of extracting metabolites from the mushroom can further comprise pressurized liquid extraction, pressurized fluid extraction, ultrasonic extraction, shock-wave extraction, microwave extraction, or ultra-turrax extraction.

After extraction, the first portion of metabolites and the second portion of metabolites can be combined. The yield of the method steps with respect to the primary and secondary metabolites present in the mushroom can be at least 80%, preferably at least 90%, based on the primary and secondary metabolites present in the mushroom. The yield of the method steps with respect to the toxins present in the mushroom can be at least 80%, preferably at least 90%, based on toxins present in the mushroom. The yield of the method steps with respect to the cyclopeptide toxins present in the mushroom can be at least 80%, preferably at least 90%, based on cyclopeptide toxins present in the mushroom.

A high-throughput process for establishing a metabolic profile of a mushroom, such as *Amanita* mushroom, can comprise extracting metabolites from mushroom using a method disclosed herein; and analyzing the extracted metabolites by automatic peak recognition or peak integration. In the high-throughput process, the extracted metabolites may be treated with one or more internal standards. The extracted metabolites can be analyzed by chromatography such as by LC, MS, LC/MS, and/or LC/MS/MS analysis. In some embodiments, the extracted metabolites may be derivatized.

An assay for identifying and/or assessing candidate metabolites extracted from *Amanita* mushroom, can comprise a) incubating the metabolites extracted from *Amanita* mushroom with an ingestible substrate under conditions suitable for feeding, wherein the metabolites are extracted using a method disclosed herein, and b) determining whether the metabolites inhibit the ingestible substrate as compared to that which has been ingested by a control substrate.

Methods of treating a subject comprising administering to the subject an effective amount of metabolites extracted from *Amanita* mushroom containing a predetermined metabolite profile, wherein the metabolites are extracted using a method described herein are also disclosed. The subject can be an animal or an insect.

The details of one or more embodiments of the invention are set forth in the accompanying drawings and the description below. Other features, objects, and advantages of the invention will be apparent from the description and drawings, and from the claims.

BRIEF DESCRIPTION OF THE FIGURE

The accompanying figure, which is incorporated in and constitutes a part of this specification illustrates aspects described below.

(FIG. 1A) methanol:water mixture (5:4, v/v); (FIG. 1B) methanol; (FIG. 1C) methanol:ethyl acetate mixture (5:4, v/v); (FIG. 1D) ethyl acetate. The amount of material extracted decreases with each extraction step. The axis scale is set by LC/MS ChemStation Software (Agilent) to optimize visibility.

FIGS. 2A-2D are chromatograms of *Amanita phalloides* samples with the extracted ions of selected cyclopeptides: (FIG. 2A) classical procedure, metabolites obtained from the first extraction; (FIG. 2B) classical procedure, metabolites obtained from completing a second, consecutive extraction on mushroom sample; (FIG. 2C) extract obtained by accelerated solvent extraction of the tissue pellet after one round of the classical procedure; (FIG. 2D) extract obtained by accelerated solvent extraction of the tissue pellet after two classical rounds. The axis scale is set by LC/MS ChemStation software (Agilent) to optimize visibility.

FIGS. 3A-3C are chromatograms showing comparison of extraction efficiency between "classic" and ASE techniques for less polar compounds; (FIG. 3A) peaks of selected less polar cyclopeptides extracted with methanol in the second step of accelerated solvent extraction; (FIG. 3B) comparison of the two techniques for less polar cyclopeptides eluting at ~22.3 min; (FIG. 3C) comparison of the two techniques for less polar cyclopeptides eluting at ~24.6 min.

FIGS. 4A-4B are graphs showing the chromatographic fingerprint of *Amanita phalloides* sample extracted using accelerated solvent extraction protocol. (FIG. 4A) peaks of commercially available standards: *α-amanitin; +β-amanitin; # phalloidin; § phallacidin; (FIG. 4B) peaks for 10 compounds surveyed in the toxin extract.

DETAILED DESCRIPTION

The materials, compounds, compositions, articles, and methods described herein can be understood more readily by reference to the following detailed description of specific aspects of the disclosed subject matter and the Examples and Figure included therein.

Before the present materials, compounds, compositions, articles, devices, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a mixture" includes mixtures of two or more such mixtures, reference to "an alcohol" includes mixtures of two or more such alcohols, reference to "the solvent" includes mixtures of two or more such solvents, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt %) or volume percent of a component, unless specifically stated to the contrary, is based on the total weight or volume, respectively, of the composition or mixture in which the component is included.

Chemical Definitions

As used herein, "peptide" refers to compounds containing two or more amino acids linked by the carboxyl group of one amino acid to the amino group of another, i.e. "peptide linkages" to form an amino acid sequence. It is contemplated that peptides may be purified and/or isolated from natural sources. A peptide may be a linear peptide or a cyclopeptide, i.e. cyclic including bicyclic.

As used herein, "cyclic peptide" or "cyclopeptide" in general refers to a peptide comprising at least one internal bond attaching nonadjacent amino acids of the peptide, such as when the end amino acids of a linear sequence are attached to form a circular peptide. A "bicyclic peptide" may have at least two internal bonds forming a cyclopeptide of the present disclosure, such as when the end amino acids of a linear sequence are attached to form a circular peptide in addition to another internal bond attaching two nonadjacent amino acids.

The peptides (including cyclopeptides) include any linear or cyclic peptide produced by a mushroom, not restricted to a biologically active toxin. It is not intended that the present disclosure be limited to a toxin or a peptide produced by an *Amanita* mushroom and includes similar peptides and toxins produced by other fungi, including but not limited to species of *Lepiota, Conocybe, Galerina*, and the like. In general, peptides from *Amanita* resembles any of the amatoxins and phallotoxins. The peptides described herein include, but are not restricted to, amatoxins such as the amanitins, and phallotoxins such as phalloidin and phallacidin. For example, an exemplary peptide in one embodiment ranges from 6-15 amino acids in length. In another embodiment a peptide toxin ranges from 7-11 amino acids in length. In one embodiment, the peptide is linear. In another embodiment, the peptide is a bicyclic peptide.

As used herein, "biologically active" refers to a peptide that when contacted with a cell, tissue or organ induces a biological activity, such as stimulating a cell to divide, causing a cell to alter its function, i.e. altering T cell function, causing a cell to change expression of genes, etc.

As used herein, the term "toxin" in general refers to any detrimental or harmful effects on a cell or tissue. As used herein, the term "toxin" in reference to a poison refers to any substance (for example, alkaloids, cyclopeptides, coumarins, and the like) that is detrimental (i.e., poisonous) to cells and/or organisms, in particular a human organism. In particular embodiments of the present disclosure, the term "toxin" encompasses toxins, suspected toxins, and pharmaceutically active peptides or biologically active peptides produced by various fungal species, including, but not limited to, a cyclic peptide toxin such as an amanitin, that provides toxic activity towards cells and humans. As used herein, a toxin encompasses linear sequences of cyclic pharmaceutically active peptides and linear sequences showing identity to known toxins regardless of whether these sequences are known to be toxic.

As used herein, "amatoxin" generally refers to a family of peptide compounds, related to and including the amanitins and includes any small peptide, linear and cyclic.

As used herein, "phallotoxin" generally refers to a family of peptide compounds, related to and including phallacidin and phalloidin.

As used herein, the term "fungi" is used in reference to eukaryotic organisms such as mushrooms, rusts, molds and yeasts, including dimorphic fungi. "Fungus" or "fungi" also refers to a group of lower organisms lacking chlorophyll and dependent upon other organisms for source of nutrients.

As used herein, "Basidiomycetes" in reference to a class of Phylum *Basidiomycota* refers to a group of fungi. "Basidiomycetes" or "*Basidiomycota*" is one of two large phyla that, together with the *Ascomycota*, comprise the subkingdom Dikarya, often referred to as higher fungi within the kingdom Fungi. Basidiomycetes include mushrooms, of which some are rich in cyclopeptides and/or toxins, and includes certain types of yeasts, rust and smut fungi, gilled-mushrooms, puffballs, polypores, jelly fungi, brackets, coral, mushrooms, boletes, puffballs, stinkhorns, etc.

As used herein, "Homobasidiomycetes" in reference to fungi refers to a recent classification of fungi, including *Amanita* spp., *Galerina* spp., and all other gilled fungi (commonly known as mushrooms), based upon cladistics rather than morphology. As used herein, "Heterobasidiomycetes" in reference to fungi refers to those basidiomycete fungi that are not Homobasidiomycetes.

As used herein, "*Ascomycota*" or "ascomycetes" in reference to members of a fungal Phylum or Division refers to a "sac fungus" group. Of the *Ascomycota*, a class "Ascomycetes" includes *Candida albicans*, unicellular yeast, *Morchella esculentum*, the morel, and *Neurospora crassa*. Some ascomycetes cause disease, for example, *Candida albicans* causes thrush and vaginal infections; or produce chemical toxins associated with diseases, for example, *Aspergillus flavus* produces a contaminant of nuts and stored grain called aflatoxin, that acts both as a toxin and a deadly natural carcinogen.

As used herein, "mushroom" refers to any material, fruiting body, mycelium, extract, tissue, etc. obtained from a fungus. As used herein, "fruiting body" refers to a reproductive structure of a fungus which produces spores, typically comprising the whole reproductive structure of a mushroom including cap, gills and stem, for example, a prominent fruiting body produced by species of *Ascomycota* and *Basidiomycota*, examples of fruiting bodies are "mushrooms," "carpophores," "toadstools," "puffballs", and the like. In some embodiments, the terms mushroom and Basidiomycetes are used interchangeably.

As used herein, "*Amanita*" refers to a genus of fungus whose members comprise poisonous mushrooms, e.g., *Amanita* (A.) *bisporigera, A. virosa, A. ocreata, A. suballiacea*, and *A. tenuifolia* which are collectively referred to as "death angels" or "Destroying Angels" and "*Amanita phalloides*" or "*A. phalloides* var. *alba*" or "*A. phalloides* var. *verna*" or "*A. verna*", referred to as "death cap." The toxins of these mushrooms frequently cause death through liver and kidney failure in humans. Not all species of this genus are deadly, for example, *Amanita muscaria*, the fly agaric, induces gastrointestinal distress and/or hallucinations while others do not induce detectable symptoms.

As used herein, the term "subject" refers to both humans and animals.

The term "sample" is used in its broadest sense. In one sense it can refer to a mushroom cell or mushroom tissue. In another sense, it is meant to include a specimen or culture obtained from any source, as well as biological and environmental samples that may comprise mushroom toxins. Biological samples may be obtained from mushrooms or animals (including humans) and encompass fluids, such as gastrointestinal fluids, solids, tissues, and the like. Environmental samples include environmental material such as mushrooms, hyphae, soil, water, such as cooking water, and the like. These terms encompass all types of samples obtained from humans and other animals, including but not limited to, body fluids such as digestive system fluid, saliva, stomach contents, intestinal contents, urine, blood, fecal matter, diarrhea, as well as solid tissue, partially and fully digested samples. These terms also refer to swabs and other sampling devices which are commonly used to obtain samples for culture of microorganisms. Biological samples may be food products and ingredients, such as a mushroom sample, a raw sample, a cooked sample, a canned sample, animal, including human, fluid or tissue and waste. Environmental samples include environmental material such as surface matter, soil, water, and industrial samples, as well as samples obtained from food processing instruments, apparatus, equipment, disposable, and non-disposable items. These examples are not to be construed as limiting the sample types applicable to the present disclosure.

As used herein, the term "biological sample" refers to any solid or fluid sample obtained from, excreted by or secreted by any living cell or organism, including but not limited to, tissue culture, bioreactors, human or animal tissue, plants, fruits, vegetables, single-celled microorganisms (such as bacteria and fungi), and multicellular organisms.

As used herein, the term "purified" or "to purify" refers to the removal of contaminants from a sample.

An "extract" or "cyclopeptide extract" as used in the present application refers to an extract obtained from a species of Basidiomycetes as defined in this application, in particular extracts obtained from the fruiting bodies and/or mycelia. An extract comprises peptides or peptide like matter. Specific peptides can be isolated from the extract. A "peptide fraction" as used in the present application is a fraction obtained from the peptide extract which is enriched in peptides compared to the peptide extract by further purification, such as chromatography.

"Yield" is defined as the measurable produce of economic value from a crop. This may be defined in terms of quantity and/or quality.

Reference will now be made in detail to specific aspects of the disclosed materials, compounds, compositions, formulations, articles, and methods, examples of which are illustrated in the accompanying Examples and Figure.

Methods

The present disclosure provides methods for the extraction and identification of metabolites comprising toxins from biological samples. The specific toxins extracted can vary. It is desirable to extract the complete metabolite profile of the specific biological sample using the methods disclosed herein. In some examples, the method can include extraction of peptide toxins, more particularly cyclopeptide toxins from a biological sample.

Unlike genetically based disease susceptibility, every human is susceptible to lethal mushroom toxins due to the direct action of toxins, primarily amatoxins, on ubiquitous cellular organelles. Furthermore, unlike poisonous plants, poisonous mushroom species are ubiquitously found throughout the world. For example, mushrooms in the genus *Amanita* section Phalloideae are responsible for more than 90% of global (worldwide) fatal mushroom poisonings. Perspectively, there are an estimated 900-1000 species of *Amanita* wherein the majority do not produce amatoxins (or phallotoxins) of which some are actually safe for humans to eat. Thus an accurate pre-ingestion determination of toxic species would prevent accidental poisoning in 100% of cases. However, there are a large number of toxin producing mushrooms commonly misidentified as an edible mushroom. Therefore, accurately detecting toxic mushrooms in the wild based upon morphology in order to avoid or identify mushroom poisoning primarily depends upon expert mycological examination of an intact mushroom.

In certain embodiments, the disclosure provides methods for the extraction and identification of metabolites from mushrooms. The metabolites can include cyclopeptides and other secondary metabolites from mushrooms, specifically peptides relating to amatoxins and phallotoxins. The particular mushrooms can be any mushroom containing cyclopeptide toxins, such as species from the genera *Amanita, Agaricus, Boletus, Lactarius, Lepiota, Russula, Tricholoma, Coprinus, Pluteus*, and others. For example, the mushrooms can be selected from *Amanita tenuifolia, Amanita bisporigera, Amanita verna, Amanita virosa, Amanita phalloides, Amanita brunnescens, Amanita ocreata, Cantharellus* spp., *Cortinarius orellanus, Chlorophyllum molybdites, Coprinus atrimentarius, Coprinus comatus; Coprinus micaceus, Entoloma lividum, Galerina autumnalis, Leucoagaricus brunnea, Lepiota josserandii, Lepiota helveola, Lepiota subincarnata, Leucocoprinus rachodes, Leucocoprinus procera, Omphalotus olearius, Paxillus involutus, Tricholomopsis platyphylla, Tricholoma pardinum, Tricholoma virgatum, Tricholoma myomyces*, and others. In specific embodiments, the mushroom can be selected from *Amanita* mushrooms. Accordingly, methods for extraction of metabolites from *Amanita* mushrooms are provided.

The specific metabolite extracted from mushroom can vary. It is desirable to extract the complete metabolite profile of the specific mushroom using the methods disclosed herein. In some examples, the method can include extraction of the complete secondary metabolic profile of the mushroom. The secondary metabolites such as mushroom peptide toxins are limited in their taxonomic distribution; for example, many species of *Amanita* make amatoxins or phallotoxins. Thus, disclosed herein are methods for extraction of amatoxins such as alpha-amanitin and phallotoxins such as phallacidin from mushrooms.

The method of extraction can include preparing a sample of the mushroom. The mushroom sample can be a solid or includes solids as a major component. In some instances, the mushroom sample can be solid particles in the absence of substantial amounts of liquid such as water. For example, the water content in the mushroom sample can be less than about 5-50% by weight, such as less than 20% by weight, or less than 5% by weight. However, most samples contain some water and may be analyzed without further treatment. For example, mushroom samples may contain up to 80 wt % water, and can be used without further treatment, or they can be dried. In a preferred embodiment, the sample can be a solid particulate. Solid samples may be ground or pulverized, using sonication or other methods known in the art, to allow better extraction of the metabolites.

After preparing the sample, a wide variety of solvents can be utilized for extraction. Generally, the metabolites are organic and may be soluble in organic solvents, water, or other aqueous solvents. The extraction solvent system can be water, an organic solvent, or a mixture thereof. Suitable organic solvents that can be used in the solvent system depend on the metabolite to be extracted. In some instances, solvent classes include, but are not limited to, $C_1$-$C_6$ alcohols, halogenated hydrocarbons, saturated hydrocarbons, aromatic hydrocarbons, ketones, ethers, alcohol ethers, nitrogen-containing heterocyclics, oxygen-containing heterocyclics, esters, amides, sulfoxides, carbonates, aldehydes, carboxylic acids, nitrites, nitrated hydrocarbons and acetamides.

As described herein, the solvent system can be a single solvent or a mixture of solvents. Generally, mixtures of solvents will contain at least two, and may contain as many as 3-10 solvents or 5-10 solvents. The solvents include, but are not limited to, water, methanol, ethanol, propanol, tetrahydrofuran, acetonitrile, methyl ethyl ketone, pentane, chloroform, N-methylpyrrolidone, cyclohexane, dimethyl formamide, xylene, ethyl acetate, chlorobenzene, methoxyethanol, morpholine, pyridine, piperidine, dimethylsulfoxide, ethoxyethanol, isopropanol, propylene carbonate, petroleum ether, diethyl ether, dioxane, perchloroethylene, isooctane (also called trimethylpentane), hexane, acetone, methylene chloride, toluene, or mixtures thereof.

In some cases, an additive can be added to the solvent system, typically to increase its solvent strength. The additives can be chosen such that ionization of the metabolites are suppressed, which allows the metabolites to become more soluble in the solvent system. Suitable additives include, but are not limited to, buffer salts, acids, and/or bases. Specific examples of additives can include trifluoroacetic acid, citric acid, acetic acid, trimethyl amine, and tetramethyl ammonium hydroxide. The additive may be present, independently, in one or more of the solvent systems used. The additive can be present in an amount of up to 5% by weight, such as from 0.01 to 5%, from 0.1 to 4.5%, or from 1 to 3.5% by weight.

The selection of the solvents to be used in the extraction of any particular metabolite can be done in several ways. For example, the chemical characteristics of the metabolite can be exploited to determine a suitable solvent system. Thus, metabolites which are known to be soluble in a particular solvent or mixture of solvents can be extracted using that solvent system. Typically, the solubility of the analyte in the solvent system should be at least about from 0.001 gm/cc to 0.5 gm/cc, although solubilities of more than about 1 gm/cc as well as lower solubilities may be acceptable. Solvents can also be chosen on the basis of their Hildebrand solubility parameters. For example, the solvents utilized can have Hildebrand solubility parameters between the parameter of pentane, 7.05, and methanol, 14.0. Hildebrand solubility parameters are known in the art; for example, Giddings et al., Science 162:67-73 (1968) contains a partial list.

Alternatively, those skilled in the art can employ other characteristics of the metabolites. For example, metabolites with known polarity can be extracted using a solvent with a compatible polarity index. Thus, a preferred embodiment utilizes solvents which have a polarity index from the polarities of pentane (polarity index of 0.0) to that of water (10.2). the polarity index of methanol is 5.1 and that of dimethyl sulfoxide is 7.2. The polarity indices of a variety of suitable solvents are found in "High Purity Solvent Guide," Burdick and Jackson Laboratories, Inc., distributed by American Scientific Products.

Alternatively, solvents can be chosen on the basis of their dielectric constant. Generally, the dielectric constant of the solvent system can range from the dielectric constant of hexane (1.88) to that of water (80.4). The dielectric constants of a variety of suitable solvents are found in "High Purity Solvent Guide," Burdick and Jackson Laboratories, Inc., distributed by American Scientific Products.

Additionally, the solvents may be chosen on the basis of their dipole moment. For example, the dipole moment of the solvent system can range from the dipole moment of trimethylpentane (iso-octane) at 0.0 Debye and of N-methylpyrrolidone at 4.09 Debye. The dipole moments of a variety of suitable solvents are found in "High Purity Solvent Guide," Burdick and Jackson Laboratories, Inc., distributed by American Scientific Products.

If the sample to be extracted contains unknown analytes, the determination of a suitable solvent system may be done in a variety of ways. For example, a sample may be divided up and extracted using different solvents. Thus, a variety of solvents can be tested; for example, a non-polar solvent, a slightly polar solvent and a highly polar solvent may all be tried. A comparison of the extracted analytes using known detection systems allows a determination of the best solvent for a particular analyte. Similar ranges may be tried based on any number of solvent and analyte properties.

In an alternative embodiment, a sample may be repeatedly extracted using different solvents, and the extracted analytes compared as above. Generally, this can be done using a series of solvents with a range of characteristics, for example non-polar, slightly polar, and highly polar solvents. Alternatively, solvents may be chosen based on different characteristics, such as polarity, dipole moment, viscosity, dielectric constant, etc. In this way a range of solvent characteristics may be tested to determine a suitable or optimum solvent for any particular analyte.

In some embodiments, the extraction can be carried out in two sequential steps. The solvent systems used in both extractions can be the same or different. For example, the solvent system used can include an aqueous solvent system or an organic solvent system. In some examples, a first solvent system selected from an aqueous solvent system can be used. The aqueous solvent system can include water alone or water mixed with an organic solvent. Preferably, the aqueous solvent system comprises water and a polar organic solvent. The polar organic solvent can include an alcohol such as methanol, ethanol, or a mixture thereof. In some cases, the solvent system comprises water and the polar organic solvent (such as methanol) in a volume ratio of from 1:5 or greater, such as 1:4 or greater, 1:3 or greater, 1:2 or greater, 1:1 or greater, 2:1 or greater, 3:1 or greater, 4:1 or greater, or 5:1 or greater. In some cases, the solvent system comprises water and the polar organic solvent (such as methanol) in a volume ratio of from 5:1 or less, 4:1 or less, 3:1 or less, 2:1 or less, 1:1 or less, 1:2 or less, 1:3 or less, 1:4 or less, or 1:5 or less. In some cases, the solvent system comprises water and the polar organic solvent (such as methanol) in a volume ratio of from 1:5 to 5:1, preferably from 1:4 to 3:1, more preferably from 1:2 to 2:1, or most preferably from 1:1 to 2:1.

In some examples, a second solvent system comprising an aqueous solvent system or a non-aqueous solvent system can be used during extraction. Preferably, a non-aqueous solvent system can be used as a second solvent system. The non-aqueous solvent system can comprise a polar organic solvent, a non-polar organic solvent, or a mixture thereof. Preferably, the non-aqueous solvent system comprises a polar organic solvent. The polar organic solvent can include an alcohol such as methanol, ethanol, or a mixture thereof. In some examples, the second solvent system consists essentially of methanol.

When two or more extraction steps are used, the steps can be carried out in any order. For example, the sample can be extracted with a first aqueous solvent system followed by a second non-aqueous solvent system. In other examples, the sample can be extracted with a first non-aqueous solvent system followed by a second aqueous solvent system. In other examples, the sample can be sequentially extracted with a first non-aqueous solvent system followed by a second non-aqueous solvent system. In other examples, the sample can be sequentially extracted with a first aqueous solvent system followed by a second aqueous solvent system. As described herein, the first solvent system and the second solvent systems can be the same or different.

Once the solvent system is chosen, extraction proceeds using a suitable extraction method. Such extraction method can be chosen from an accelerated solvent extraction, pressurized liquid extraction, pressurized fluid extraction, ultrasonic extraction, shock-wave extraction, microwave extraction, or ultra-turrax extraction. Preferably, an accelerated solvent extraction method is used.

The accelerated solvent extraction methods can proceed as follows. First, an extraction cell can be loaded with a mushroom sample containing the metabolite or metabolites of interest. The sample may substantially fill the cell, that is, the dead volume of the cell is kept to 10% or less, although in some cases, compression of the sample during extraction may occur, causing a dead volume to occur. However, the void volume of the sample may be higher than 10%. This filling of the extraction cell allows uniform flow through the sample with high yields of extraction. Thus, the size of the extraction cell preferably is chosen to allow the sample to fill the cell completely. Suitable extraction cells can have volumes of 0.5 ml to 50 ml, such as 5 ml, 10 ml, 15 ml, 15 ml, or 25 ml. The extraction cells can be constructed of materials which allow the use of high pressures and temperatures. Suitable extraction cells include cells used in supercritical fluid extraction, and generally have frits of some type to retain the sample in the cell, as will be appreciated by those skilled in the art.

In alternative embodiments, the volume of the sample is less than the volume of the extraction cell, and an inert filler is used to load the extraction cell to capacity. In some cases, inert fillers may be used if the sample is highly compressible, which can lead to clogging of the system. Suitable inert fillers include solid particulate substances which do not contain extractable materials, such as sand, diatomaceous earth or glass wool. Other inert fillers will be readily ascertainable by those skilled in the art.

Once the extraction cell is loaded with sample, it can be attached via its inlet and outlet ports to the pump and the sample collection vial. In one embodiment, the extraction cell is placed within a preheated oven or heating block and allowed to equilibrate to the oven or block temperature with a preferred equilibration time of 5 to 15 minutes. Alternatively, the solvent may be preheated to the desired temperature prior to contact with the sample. Also, the solvent and the sample may both be preheated. Preheating of either sample or solvent is not necessary, as outlined below.

Once the cell containing the sample is loaded and optionally preheated, the extraction may proceed in two ways, either with a static extraction step or in a dynamic, flow through mode.

A static extraction step is preferred. In this method, the solvent is pumped into the extraction cell with a static valve open, flow is established through the cell and a small amount, usually about 1 ml, is collected at the outlet. The valve is then closed, and the system is pressurized to the appropriate pressure. Suitable pressures will depend on the particular solvents and samples of the run; for example, samples with high levels of extractable materials generally require less pressure. Suitably, the pressure ranges from about 100 to about 2500 psi. For example, the pressure can range from about 1000 to about 2000 psi, or up to about 2000 psi.

Once the valve is closed, the extraction cell is placed in the oven and the sample is brought up to temperature. As for the temperature, the exact temperature to be used will depend on the solvents and the metabolites. Generally, the temperature in ° K is maintained at a level of about 0.8 to 2.0 times the average boiling point in ° K of the solvent system under standard conditions. A preferred temperature in ° K ranges from about 1.0 to about 2.0 times the average boiling point, with the most preferred range being between about 1.0 to about 1.6 times the average boiling point.

The average boiling point in either ° K or ° C. can be determined using techniques known in the art. If the solvent system comprises a single solvent, the boiling temperature is ascertainable by reference to standard chemical charts. If the solvent system comprises two or more solvents, the average boiling temperature under standard conditions (at atmospheric pressure) can be readily determined using techniques known in the art.

The temperatures and pressures used in the method of the present methods are below supercritical conditions. That is, the solvent systems are in liquid form prior to extraction, at standard temperatures and pressures such at 25° C. and atmospheric pressure. In addition, the solvents remain liquid during extraction, due to the pressures used during extraction. Thus, even if the temperature is above the boiling point of the solvent system used, the solvent system remains liquid during extraction.

Preferably, the extraction can be carried out at a temperature from 50° C. or greater, 60° C. or greater, 70° C. or greater, 80° C. or greater, 90° C. or greater, 100° C. or greater, 110° C. or greater, 115° C. or greater, 120° C. or greater, 125° C. or greater, 130° C. or greater, 140° C. or greater, or 150° C. or greater. In some embodiments, the extraction can be carried out at a temperature from 200° C. or less, 190° C. or less, 180° C. or less, 170° C. or less, 160° C. or less, 150° C. or less, 140° C. or less, 130° C. or less, 120° C. or less, 110° C. or less, 100° C. or less, 90° C. or less, or 80° C. or less. In some embodiments, the extraction can be carried out at a temperature from from 50° C. to 200° C., such as from 80° C. to 160° C., from 85° C. to 150° C., from 100° C. to 130° C., or from 110° C. to 130° C.

The cell is kept under pressure and temperature for a period of time. When the extraction is run without a preheat step, the time of extraction includes the time it takes for the extraction cell and sample to reach the target temperature. Generally, it takes the cell about 5 minutes to reach the target temperature, although longer or shorter times may be necessary depending on the system used. After the cell has reached the target temperature, extraction proceeds for sufficient time to extract at least a portion of at least one of the analytes from the sample. Generally this time ranges from about 5 minutes to 30 minutes, with the preferred time being from about 5 minutes to about 15 minutes, and the most preferred time being from about 5 to about 10 minutes. Under certain circumstances, extraction times of up to an hour may be required.

The time sufficient to extract the metabolites from the sample may be determined in several ways, and will depend in part on the purpose of the extraction. For example, if qualitative identification of analytes is of primary importance, then a less efficient extraction may be done. Alternatively, if the quantitation or yield of the analytes is important, a more complete extraction is desirable.

In some embodiments, the extraction is run such that not more than about 20%, and preferably not more than 10%, more of the metabolite or metabolites will be subsequently extracted in a subsequent extraction using the same method or other extraction methods such as Soxhlet or microwave extraction. Thus, the time of extraction is chosen such that at least about 80-100% of the extractable analytes are extracted. Generally, as outlined above, this time ranges from 5 to 30 minutes for the average sample. One measure of sufficient extraction is that no more than about 10% more of the analytes would be extracted by maintaining the same extraction conditions for an additional hour. As will be appreciated by those skilled in the art, sample extraction may be discontinuous. In that event, the time is the total time of extraction.

In a preferred embodiment, when the sample is a solid matrix, it is not dissolved during extraction, but rather the analytes removed. Thus the conditions of the reaction are designed to avoid the complete solubilization of a solid matrix. However, as one skilled in the art will appreciate, solid matrices containing significant amounts of metabolites may show a decrease in mass as a result of the extraction of the metabolites.

Once the static time is complete, the static valve is opened, a volume of flush fluid (approximately 1 to 5 ml) is pumped into the cell. The flush fluid is a liquid solvent which is introduced into the cell, prior to removing the solvent system containing the extracted metabolites, to minimize analyte loss in the removal step. The flush fluid may be the same solvent system used in the extraction, or another liquid solvent. A purge fluid i.e. a fluid which will displace the solvent system containing the extracted analytes from the sample, is introduced to drive the solvent containing the analytes out of the extraction cell into a collection vial. The collection vial may be under pressure, or may be at atmospheric pressure. The vial may be unsealed, or sealed and under an atmosphere of air or inert gas, such as the one used as the purge fluid. The purge fluid may be an inert gas, such as helium, nitrogen or carbon dioxide, or in some circumstances it may be another solvent. Alternatively, the purge fluid may be the same solvent system as used in the extraction. The lines may then be flushed with fresh solvent and the extraction cell is removed and cleaned for the next use. Static extraction may be repeated oen or more times if desired, such as two times, three times, four time, up to ten times.

The amount of solvent needed to extract the analytes using the methods described herein will vary. Generally, the amount of solvent used is kept to a minimum, and is usually the amount of solvent contained within the cell during extraction, i.e. the solvent in the void volume. Suitably, the ratio of the volume of solvent to the volume of the extraction cell ranges from 1:1 to 5:1, preferably in the ratios of 1.2:1, 1.5:1, 2:1, 3:1 and 4:1. In an alternative embodiment, when the sample fills the cell, the ratio of the volume of solvent to the volume of the sample ranges from 1:1 to 5:1, with 1.2:1, 1.5:1, 2:1, 3:1 and 4:1 also preferred. Similarly, the ratio of the volume of the solvent to the weight of the sample typically falls in the range of from about 1:1 in ml/gm to 5:1 ml/gm.

In an alternative embodiment, the extraction is performed in a dynamic, flow-through mode. In this embodiment, the loading of the extraction cell and pressurization of the cell proceeds as above. In this case, a preheating step prior to the introduction of the solvent is preferred. After preheating, solvent is flowed slowly through the cell and collected. Those skilled in the art will appreciate that the faster the flow rate, the less efficient the extraction, but that higher flow rates may be appropriate for larger extraction cells or samples with large quantities of extractable material. Thus generally the flow rates range from about 0.1 to about 5 ml/minute, with a preferred range from about 0.1 to about 0.5 ml/min, when the cell volume is 0.5 to 10 ml. In this embodiment, the total volume of the solvent needed for the extraction ranges from about twice the volume of the extraction cell to about five times the volume of the extraction cell.

In an alternative embodiment, both static and dynamic extraction may be done. For example, the system may have a static step, followed by a flow through step. This may be repeated several times if desired.

When multiple extraction steps are used, the metabolites dissolved in the solvent (such as a first portion of metabolites and a second portion of metabolites) can be combined. As described herein, the extraction is run such that at least about 80-100% of the extractable analytes are extracted. In some embodiments, the combined metabolites can comprise at least 80% by weight, preferably at least 90% by weight, more preferably substantially all the primary and secondary metabolites from the *Amanita* mushroom. In some embodiments, the combined metabolites can comprise at least 80% by weight, preferably at least 90% by weight, more preferably substantially all toxins from the *Amanita* mushroom. In some embodiments, the combined metabolites can comprise at least 80% by weight, preferably at least 90% by weight, more preferably substantially all cyclopeptide toxins from the *Amanita* mushroom.

The yield of the method steps with respect to the primary and secondary metabolites present in the mushroom can be at least 80%, preferably at least 90%, based on the primary and secondary metabolites from the mushroom. The yield of the method steps with respect to the toxins present in the mushroom can be at least 80%, preferably at least 90%, based on toxins from the mushroom. The yield of the method steps with respect to the cyclopeptide toxins present in the mushroom can be at least 80%, preferably at least 90%, based on cyclopeptide toxins from the mushroom.

Further, once the metabolites dissolved in the solvent are obtained, they are usually detected or analyzed. This may be done in a variety of ways, depending on whether identification or quantification of the metabolites is desired, and on the composition of the metabolites. The metabolites may be retained in the solvent, or the solvent removed, for example by evaporation. Generally, the metabolites are analyzed using techniques well known in the art, including, but not limited to, application of gas chromatography, mass spectrometry, ion chromatography, liquid chromatography, capillary electrophoresis, liquid chromatography/mass spectrometry, gas chromatography/mass spectrometry, and/or liquid chromatography/mass spectrometry/mass spectrometry. In addition, the solvent system containing the metabolites may be concentrated prior to analysis, for example by inert gas blow-down or evaporation. If the concentration of metabolites is high, the metabolites may also be diluted prior to analysis by adding solvent, for example.

The methods described herein can be used in a high-throughput process for establishing a metabolic profile of mushrooms such as *Amanita* mushroom. The high-throughput process can include extracting metabolites from the mushroom using a method described herein and analyzing the extracted metabolites by automatic peak recognition or peak integration. In some embodiments, the extracted metabolites can be treated with one or more internal standards. In some embodiments, the extracted metabolites can be analyzed by chromatography as described herein. The extracted metabolites can be derivatized for analysis.

The methods described herein can be used for identifying and/or assessing candidate metabolites extracted from mushrooms, such as *Amanita* mushroom. The process can include incubating the metabolites extracted from *Amanita* mushroom containing a predetermined metabolite profile with an ingestible substrate under conditions suitable for feeding, and determining whether the metabolites inhibit the ingestible substrate as compared to that which has been ingested by a control substrate.

Methods of inhibiting a cell are also provided herein. The method can include contacting the cell or administering to a subject comprising the cell an effective amount of metabolites extracted from *Amanita* mushroom, wherein the metabolites are extracted using a method described herein. The extracted metabolites can contain a predetermined metabolite profile. The subject can be an animal such as an insect.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures and other reaction ranges and conditions that can be used to optimize the product purity and yield obtained from the described process. Only reasonable and routine experimentation will be required to optimize such process conditions.

Example 1: Development of an Exhaustive Extraction Protocol for Cyclopeptides and Other Secondary Metabolites in *Amanita phalloides* with Recommendations of Best Practices when Using Natural Product Extracts in Feeding Assays Plants and fungi contain a variety of biologically active compounds. However, many experiments characterize the effects of only a single metabolite or a subset of these compounds on the animals that ingest them. This example investigates mushroom-feeding *Drosophila* and the metabolites of their host *Amanita phalloides*. An extraction protocol that recovers all mushroom secondary metabolites has been provided and recommendations for the best practices when using natural extracts in feeding assays are discussed.

Introduction. *Amanita phalloides* mushrooms (Death Caps) contain a mixture of cyclopeptide toxins that are the source of the mushroom's toxicity. Within *A. phalloides*, 14 amatoxins and phallotoxins occur (Table 1), and both the tissue type and life stage of the mushroom influence the concentration of these toxins. For example, determined that α-amanitin constitutes 17% of the toxin load in the cap, but only 8.8% of the toxin load in the bulb.

TABLE 1

Cyclopeptide toxins previously identified in *Amanita phalloides* mushrooms. Includes the toxin subclass, molecular weight, and source that reported the occurrence.

| Subclass | Toxin | Molecular Weight |
|---|---|---|
| Amatoxin | α-amanitinad[a,b] | 918.97 |
| | β-amanitin[a,b] | 919.954 |
| | γ-amanitin[b] | 902.970 |
| | δ-amanitin[b] | Structure Unknown |
| | ε-amanitin[b] | 903.962 |
| | Amanin[b] | 903.962 |
| | Amanullin[b] | 886.979 |
| Phallotoxin | Phalloidin[a,b] | 788.868 |
| | Phalloin[b] | 772.868 |
| | Phallisin[b] | 804.867 |
| | Prophalloin[c] | 756.869 |
| | Phallacidin[a,b] | 846.904 |
| | Phallacind[d,e] | 830.904 |
| | Phallisacin[a,d] | 862.903 |

[a]Toxins found in highest concentrations in *A. phalloides* (Enjalbert et al., 1992)
[b](Wieland, 1968)
[c](Munekata et al., 1978)
[d](Faulstich et al., 1975)
[e](Wieland, 1983)

While *A. phalloides* and other mushrooms that contain cyclopeptides are lethal to many eukaryotic organisms, 17 mushroom-feeding *Drosophila* species use these toxic mushrooms as developmental hosts along with other non-toxic *Basidiomycota* mushrooms. Little is known about cyclopeptide tolerance in these fly species, but their toxin tolerance is not due to mutations in RNA polymerase II that would prevent the toxin binding. Thus far, studies examining cyclopeptide tolerance in the mushroom-feeding *Drosophila* focused exclusively on α-amanitin. In this example, toxin tolerance using feeding assays that more closely resemble to the wild mushrooms were characterized. In this example, 1) the development of an exhaustive extraction protocol for cyclopeptides and other secondary metabolites in *Amanita phalloides* is provided, 2) recommendations of best practices when utilizing natural product extracts in feeding assays based on the present study of toxin tolerant *Drosophila* and natural extracts of *A. phalloides* is proposed, and 3) the conserved fragmentation pattern of cyclopeptides found in these mushrooms is detailed.

Materials and Methods

Mushroom collection, drying and storage conditions: *A. phalloides* used in this example was collected at Bolinas Ridge in Nicasio, Calif. (GPS: 38.042664, −122.784958). The identity of the mushrooms was confirmed by Trent Pearce (Naturalist at East Bay Regional Park). The mushrooms were sliced into pieces approximately 6 mm thick, and then dried in a Fisherbrand Isotemp General Purpose Heating and Drying Oven at 60° C. The dried mushrooms were stored in a sealed plastic bag at 4° C. Vouchers of these samples were stored at 4° C. in a lab at the University of Alabama.

Accelerated solvent extraction: Accelerated solvent extraction (ASE) is an innovative technique using optimized and controlled temperature and pressure conditions to enhance the extraction of numerous solid and semisolid matrices. The enhanced yields are obtained by completing the extraction at temperatures exceeding the solvent's boiling point by utilizing increased pressure. Furthermore, the extraction is a fully controlled process, which eliminates the problem of batch to batch variability caused by changing extraction conditions. Thus, ASE is a fast, efficient, and more environmentally friendly approach and has been proven to be a reliable and reproducible extraction technique for numerous types of natural matrices.

In the present ASE approach, the ground mushroom tissue (~100 mg) was mixed with sand to allow proper dispersion of the substrate material. Subsequently, the material was loaded into the 34 ml extraction cell and the sample was extracted first with methanol:water mixture (5:4, v/v) followed by pure methanol. The optimal extraction parameters were determined by testing solvent type (water, methanol, ethyl acetate, n-hexane), oven temperature (range between 90 and 140° C.), number of static cycles (from 1 to 3 cycles), and static time (5 min; 10 min) to acquire the maximum yield in minimal time. The following ASE parameters were used during both steps in one example: oven temperature: 120° C., static time: 5 mins; static cycles: 1; rinse volume: 50%. Four solvents differing in polarity were used to extract compounds with various physicochemical properties. When using ASE, the polarity of solvent can vary depending on the temperature and pressure used. For example, water, a polar solvent has been shown to be also suitable to extract less polar components from solid matrices when using ASE. All the extracts obtained with different solvents were monitored using HPLC-DAD-MS, which allowed to determine the optimal conditions required to extract compounds with varying physicochemical properties.

"Classic" approach: The "Classic" approach follows the following methodology. The ground tissue (~100 mg) was placed in a 15 ml Falcon Tube (VWR), and 5 ml of the extraction solvent (methanol:water:0.01 M HCl 5:4:1 v/v) was added. The tube was incubated overnight at room temperature on a shaker plate. Following the incubation period, the tube was centrifuged for 5 min at 10,000 g. The supernatant was decanted into a round—bottom flask and dried down in a rotary evaporator. It was then resuspended in 2 ml 1:1 methanol:water, transferred to a 2 ml microcentrifuge tube and dried down in a vacuum centrifuge. The resulting solids were resuspended in 1 ml of Millipore water. The reconstituted sample was characterized using HPLC-MS (protocol detailed below). The impact of repeating this procedure on the same tissue pellet by resuspending the pellet in a second volume of extraction solvent (15 ml) after the initial extraction was assessed. The pellet was again incubated at room temperature on a shaker plate, and the extraction protocol was repeated exactly 24 hr later.

HPLC-MS Conditions:

The *A. phalloides* extracts were analyzed using Agilent 1260 Infinity II system, comprised of an Infinity II Binary Pump, Infinity Multisampler, Multicolumn Thermostat, Diode Array Detector (DAD, UV spectrometer), Agilent's Instrument Control Framework, and Mass Selective Detector (MSD, mass spectrometer). The analysis was performed using Pursuit 5C18 150×4.6 mm column at 23° C. The mobile phase comprised (A) water containing 0.2% formic acid, and (B) acetonitrile containing 0.2% formic acid. The following elution gradient was applied: 0-4 min 10% B; 4-20 min 10%-55% B; 20-25 min 55% B; 25-30 min 55%-100% B; 30-33 min 100% B; 33-35 min 100%-10% B; 35-40 min 10% B. Five microlitre of the extract was injected onto the column and run at a 1.0 ml/min mobile phase flowrate. The eluate was monitored by DAD at 214 and 295 nm, and UV-VIS spectra within the range of 190-400 nm were stored for all the peaks. All the samples were analyzed on the MSD in electrospray positive ionization mode with 10 L/min drying gas flow rate, 50 psig nebulizer pressure, 350° C. drying gas temperature, and 4,000 V capillary voltage. For fingerprinting, full scan acquisition mode was used with scan range: 100-1,200.

Quantitative Analysis of Cyclopeptide Markers:

Standard samples of α-amanitin, β-amanitin, phalloidin and phallacidin were obtained from SantaCruz Biotechnology and Cayman Chemical. They were dissolved in double-distilled water (α-amanitin, β-amanitin) or methanol (phalloidin, phallacidin) at a concentration of 1 μg/μl. These stock solutions were subsequently diluted ten-fold and used to confirm identification of selected cyclopeptides in the analyzed extracts.

Results

Figure 1A:
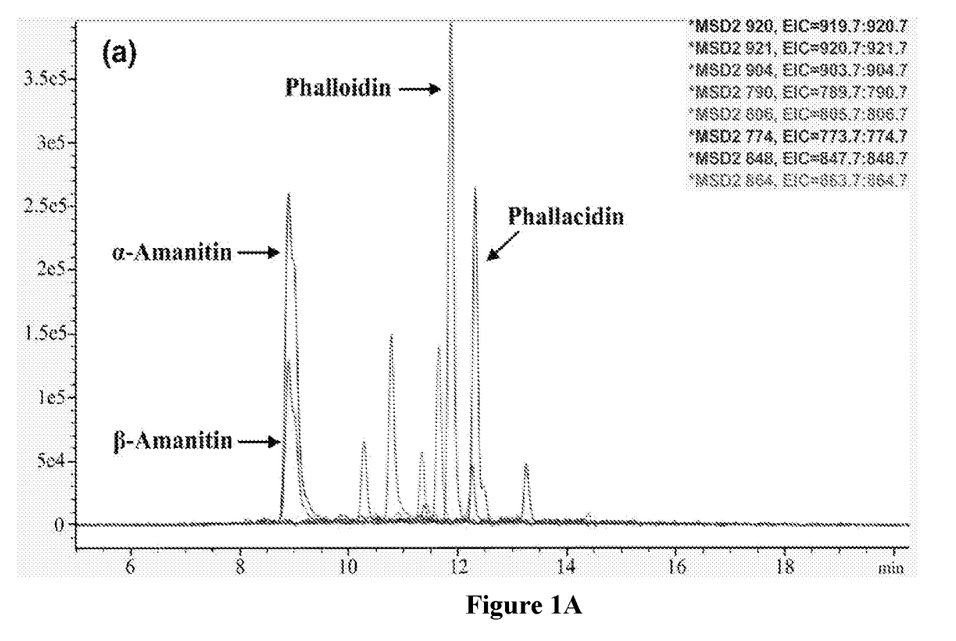
FIGS. 1A-1D are chromatograms of *Amanita phalloides* samples with the extracted ions of selected cyclopeptides obtained after each consecutive accelerated solvent extraction step using the following solvents or solvent mixtures in sequence.
Figure 1B:
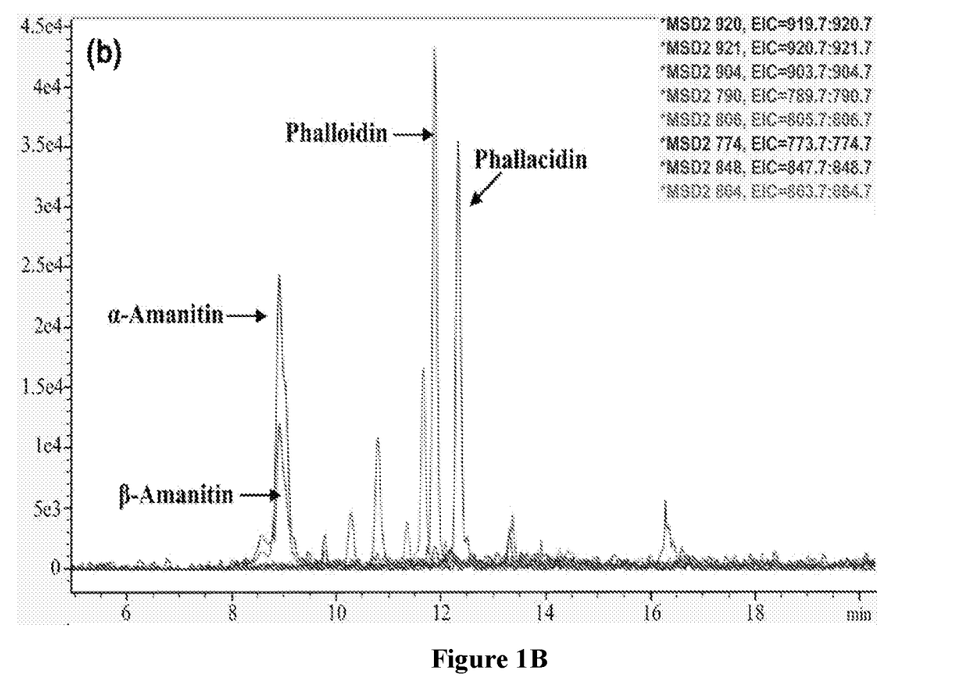
Figure 1C:
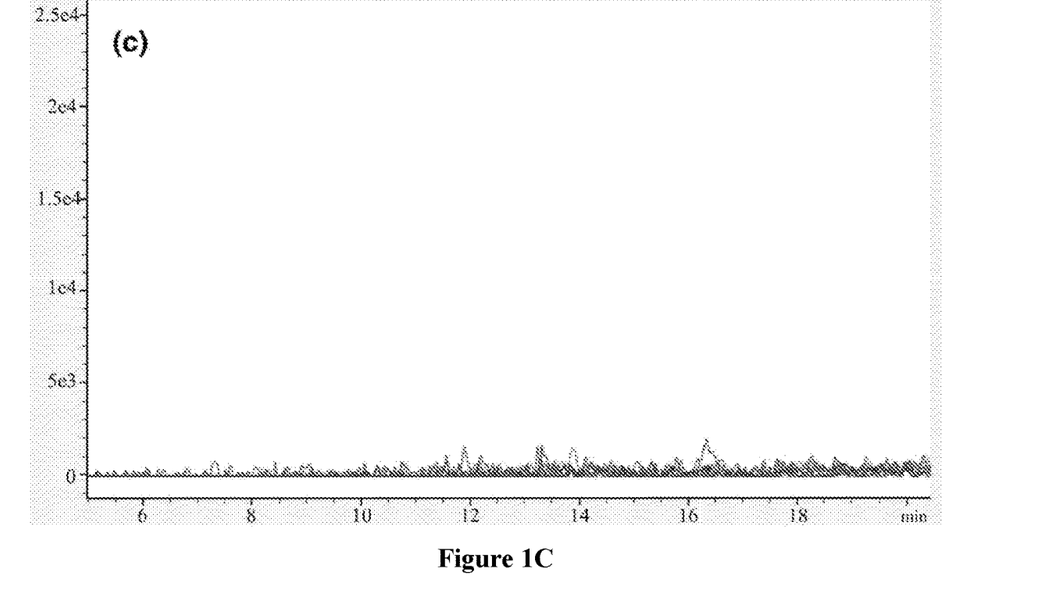
Figure 1D:
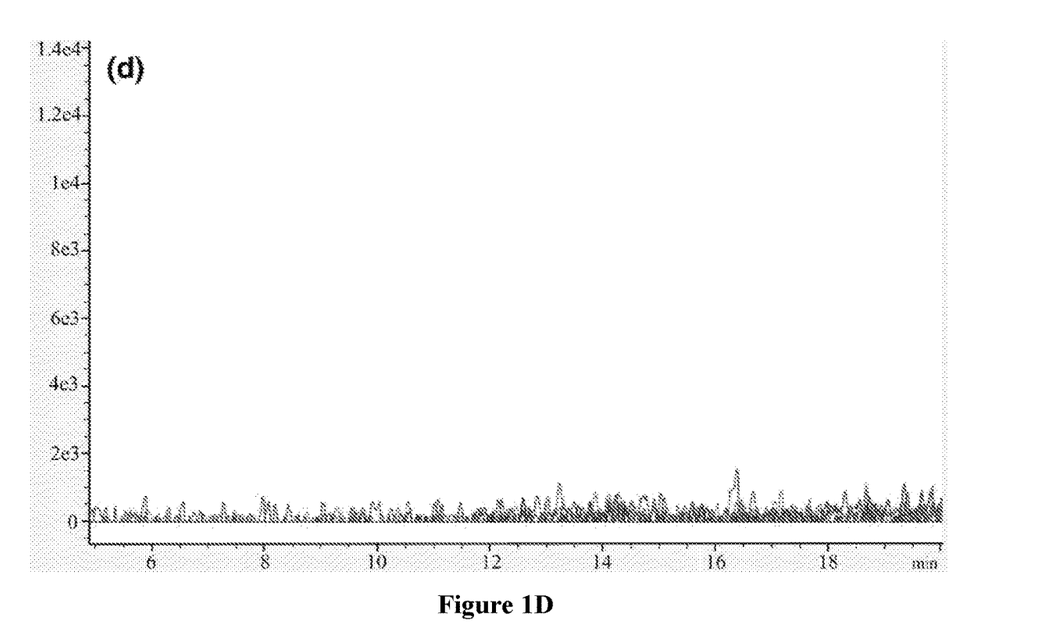
Figure 4A:
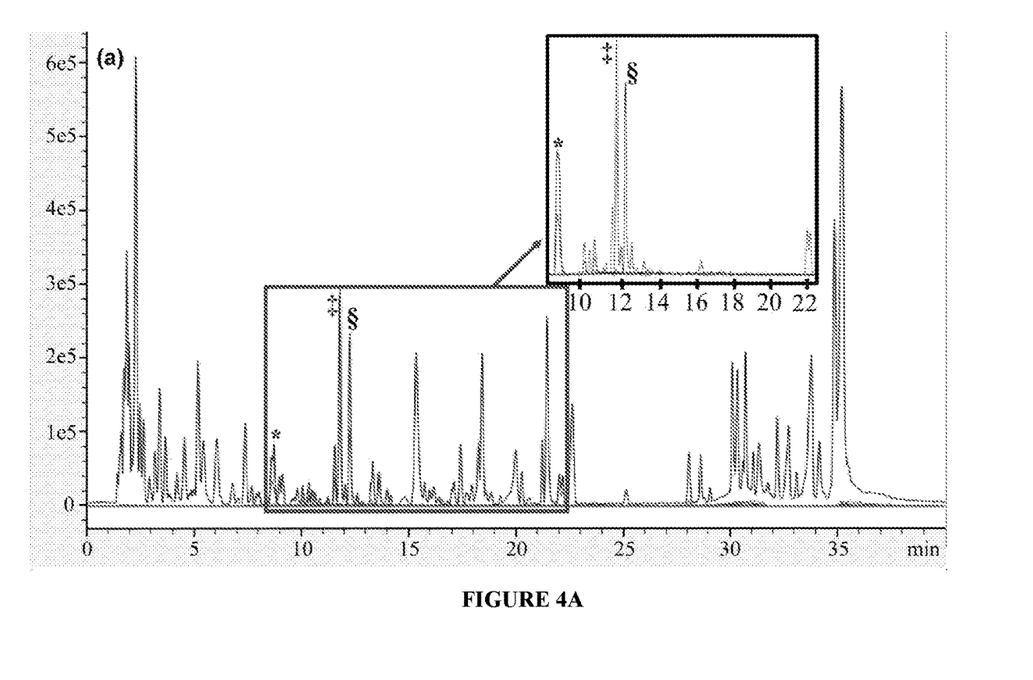

Accelerated Solvent Extraction Optimization:

in the present example, the innovative sample preparation technique, accelerated solvent extraction (ASE), was used to extract secondary metabolites from the *A. phalloides* mushroom samples. The following ASE parameters were found as optimal and used during both accelerated solvent extraction steps: oven temperature—120° C.; static time—5 min; static cycles—1; rinse volume—50%. It was found that running two consecutive optimized cycles per sample with increasingly less polar solvents (i.e., 5:4 methanol:water followed by pure methanol) resulted in exhaustive extraction of polar toxins as well as less polar metabolites (FIGS. 1A, 1B). Additional consecutive rounds of extraction with increasingly less polar solvents (5:4 methanol:ethyl acetate and ethyl acetate) did not recover additional metabolites (FIGS. 1C,1D). All of the known cyclopeptides eluted between 8 and 14 minutes (FIG. 4A).

Figure 2A:
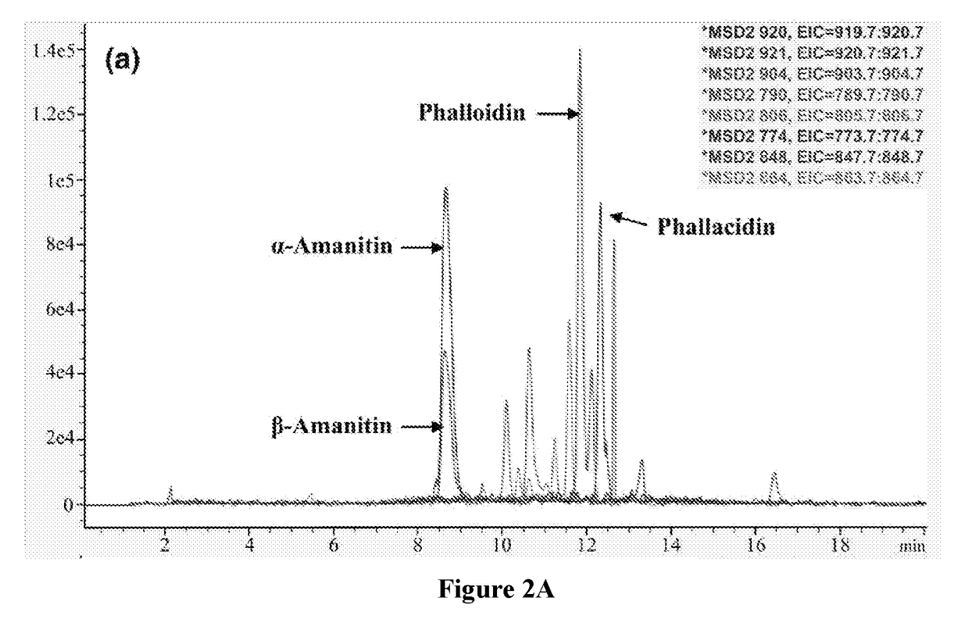
Figure 2B:
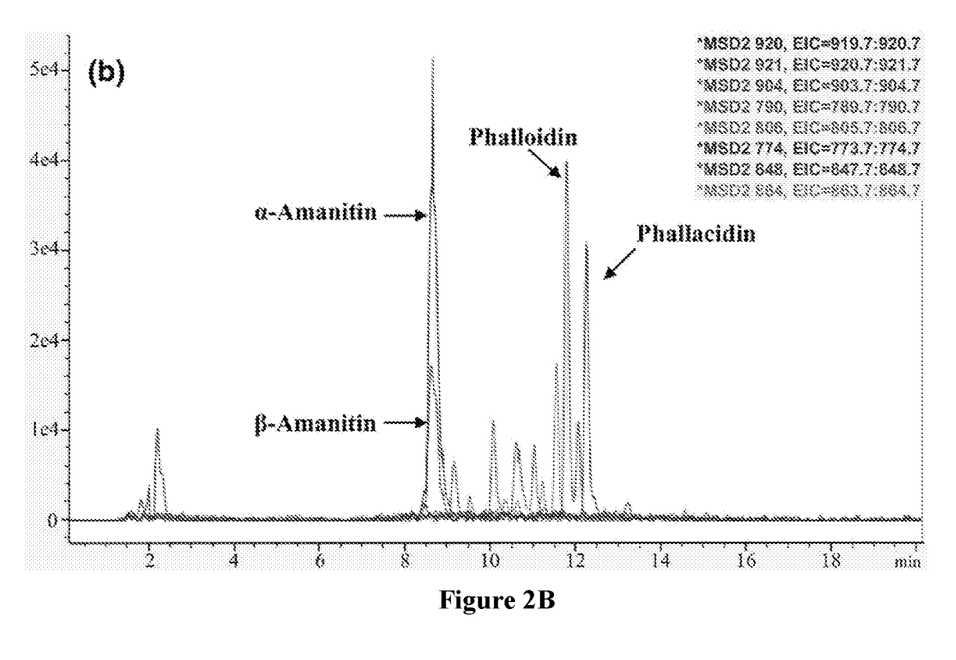
Figure 2C:
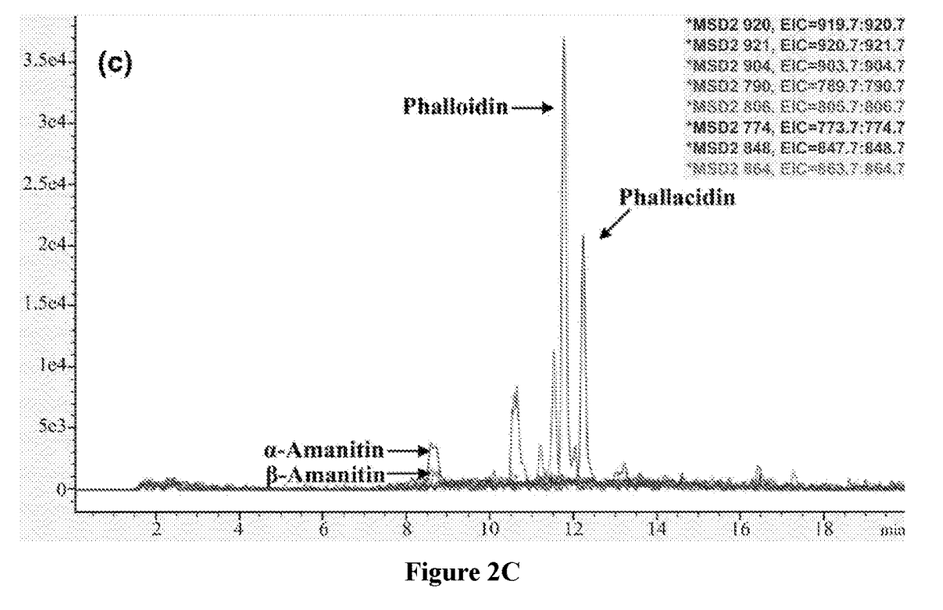
Figure 2D:
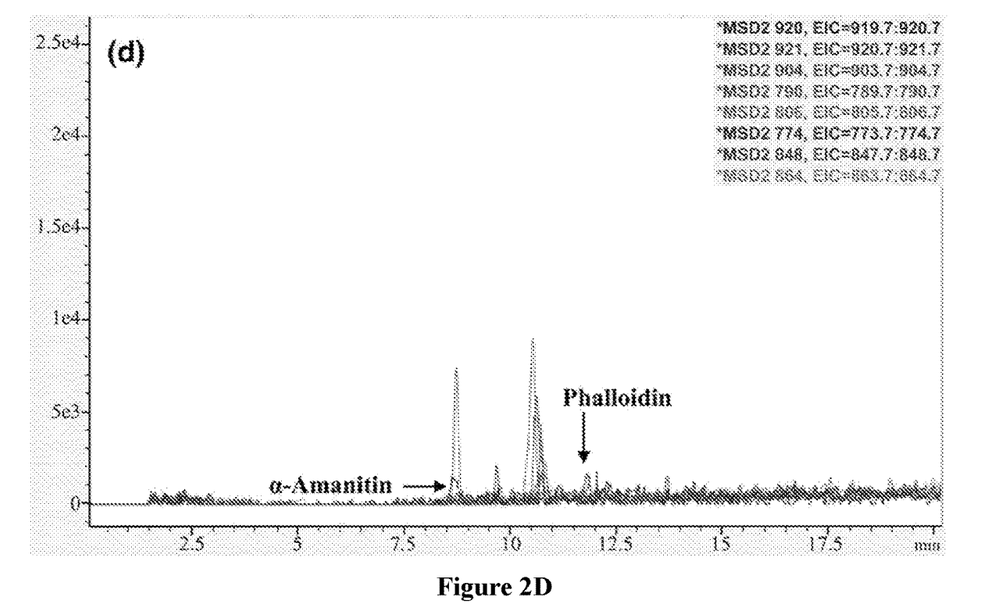

Some applications using the "Classic" extraction protocol repeat the extraction procedure twice on a single sample. Therefore, two consecutive rounds of the "Classic" extraction method were completed on a mushroom sample and then the remaining mushroom tissue extracted a third time using the ASE approach. It was found that the extract from the second cycle of the "Classic" approach also contained substantial amounts of cyclopeptides (FIG. 2B), and measurable quantities of the cyclopeptides were still recovered by ASE extraction (FIG. 2D).

Figure 3A:
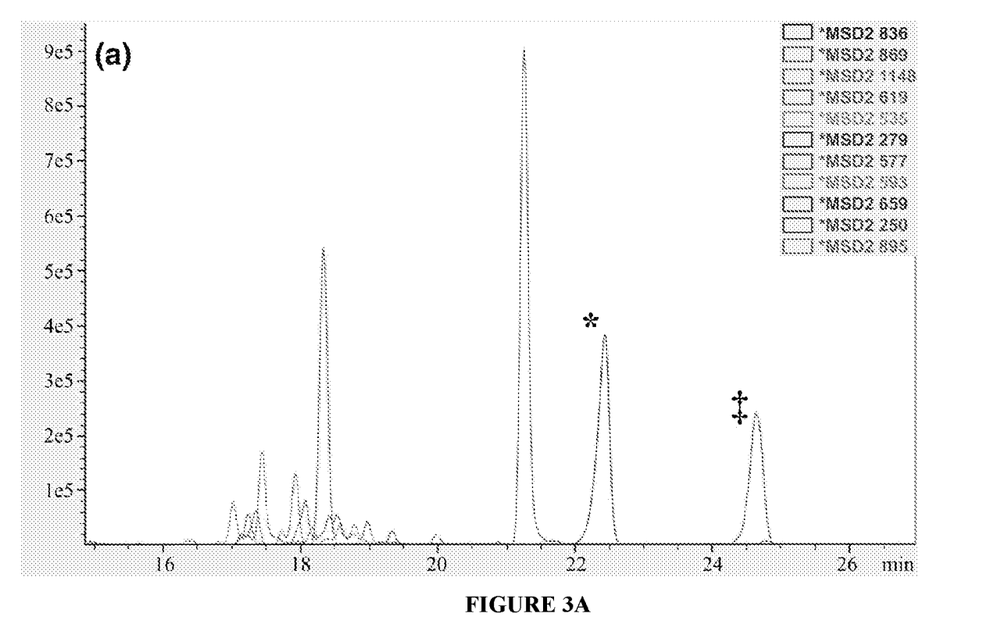
Figure 3B:
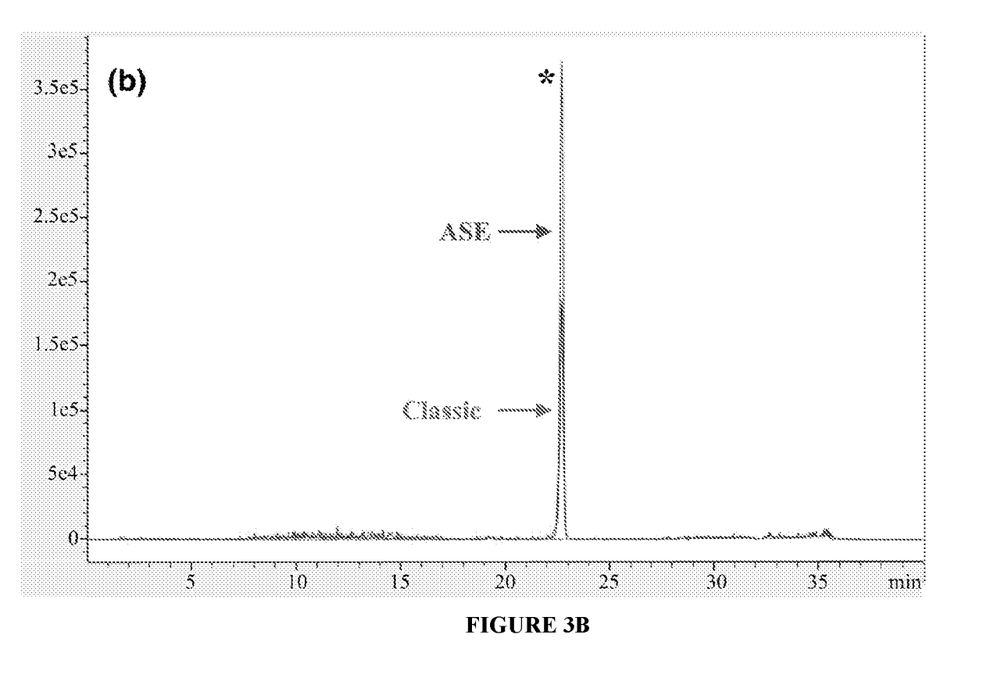
Figure 3C:
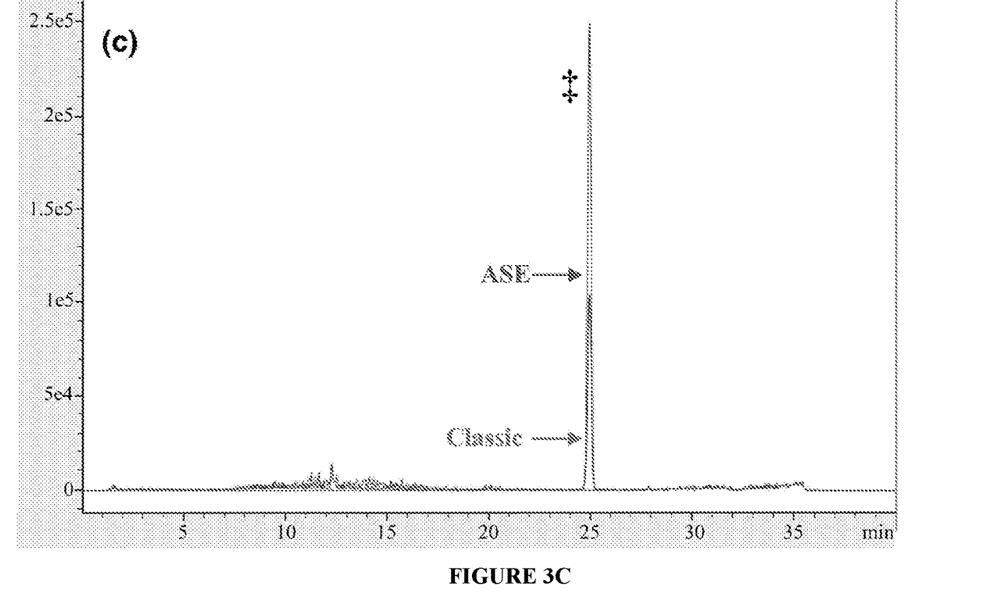

The solvents used in the "Classic" method (i.e., methanol: water:0.01 M HCl 5:4:1 v/v) are optimized for the isolation of more polar cyclopeptides (e.g., α-amanitin). In addition to exhaustively extracting the polar toxins, it was found that ASE extraction protocol isolated almost double the amount of less polar compounds than the "Classic" procedure (FIGS. 3A-3C).

Discussion: extraction protocols for α-amanitin and other cyclopeptides have been previously described. However, these methods focus on extraction of only polar cyclopeptides by incubating macerated mushroom tissue for 12 to 24 hours in aqueous-methanolic solutions with the addition of mineral or organic acid (e.g., hydrochloric or formic acid). Some protocols call for re-extraction of the remaining pellet extending the procedure to 48 hours. The prior art procedure was compared to the ASE procedure. The prior art procedure demonstrated that even following double extraction of the mushroom samples with this 'Classic' approach was not exhaustive. Furthermore, the extract resulting from the 'Classic' protocol represented only the polar fraction of metabolites and misrepresents more lipophilic metabolites. These less polar compounds, such as antamanide, a possible antitoxin for some *Amanita* cyclopeptides, could alter the observed biological effect of the complete suite of secondary metabolites relative to a single metabolite of interest (e.g., α-amanitin), Thus, these data indicate that previous reports may have underestimated the amount of amanitin and other toxins in mushroom tissue.

The results of the present example demonstrate the use of ASE for the extraction of many classes of secondary metabolites. This is believed to be the first report on exhaustive extraction of cyclopeptides and other metabolites from *Amanita* samples. The optimized ASE procedure significantly shortened the process of sample preparation preceding feeding assays. The use of ASE provided extracts more closely resembling the chemical complexity of real samples. ASE can be easily optimized for any type of solid matrices and improve batch to batch reproducibility, Thus, ASE could be used in a broad range of ecological experiments examining different plant-insect interactions.

Figure 4B:
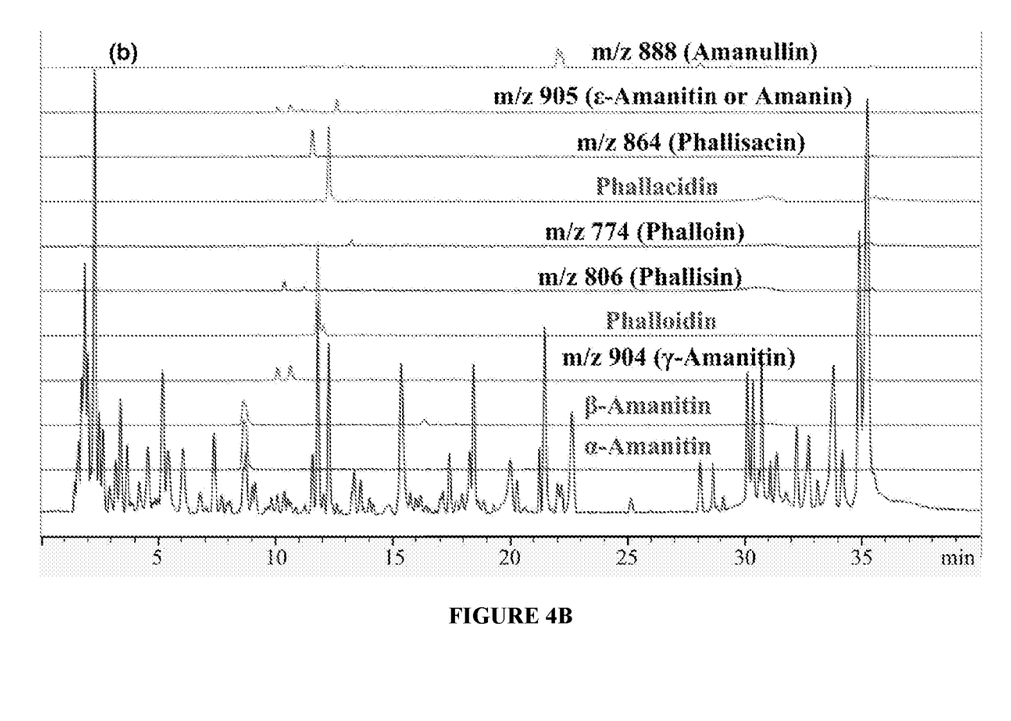

Feeding Assay Best Practices:

In order to maximize reproducibility of the present example and using host secondary metabolite extracts in experiments examining plant-insect interactions, the following are preferred. (a) When a host secondary metabolite extract is used within an experiment, include details of the manner in which the extract was produced. Some points to identify include where, when, and how tissue samples were originally gathered, whether the natural products were extracted from fresh, frozen, or dried material, the method used to prepare the sample for extraction, the extraction protocol and its parameters, and the method of storage following extraction. (b) Following the production of the secondary metabolite extract, it should be fingerprinted prior to use. Fingerprinting the sample can be done using markers of compounds known to occur in the extract, which allows for the identification and quantification of the amounts of different metabolites. In the present example, four commercially available standards for cyclopeptides (FIGS. 4A-4B) were used. The full fingerprint of the analyzed extract demonstrates the complexity of the sample, a factor that has not been addressed in previous studies of toxin tolerance. Furthermore, having a fingerprint of previous sample extracts makes it possible to compare different batches. These comparisons can then be used to determine whether the extracts differ significantly. (c) To maximize consistency, the manner in which the secondary metabolite extract will be used in an experiment should be specified. By using the extract as opposed to fresh host tissue, it is possible to control the quantities of the different metabolites to which the insects are exposed.

The materials and methods of the appended claims are not limited in scope by the specific materials and methods described herein, which are intended as illustrations of a few aspects of the claims and any materials and methods that are functionally equivalent are within the scope of this disclosure. Various modifications of the materials and methods in addition to those shown and described herein are intended to fall within the scope of the appended claims. Further, while only certain representative materials, methods, and aspects of these materials and methods are specifically described, other materials and methods and combinations of various features of the materials and methods are intended to fall within the scope of the appended claims, even if not specifically recited. Thus a combination of steps, elements, components, or constituents can be explicitly mentioned herein; however, all other combinations of steps, elements, components, and constituents are included, even though not explicitly stated.

What is claimed is:

1. A method for extracting metabolites from mushroom comprising:
    a) mixing a sample of the mushroom with sand;
    b) contacting the sample with a first solvent system in an extraction cell at a temperature of 80° C. or greater for a sufficient time to extract at least a first portion of metabolites from the sample; and
    c) contacting the sample with a second solvent system in an extraction cell at a temperature of 80° C. or greater for a sufficient time to extract at least a second portion of metabolites from the sample;
    wherein the first portion of metabolites and the second portion of metabolites include primary and secondary metabolites from the mushroom.

2. The method of claim 1, wherein the mushroom is selected from any mushroom containing cyclopeptide toxins.

3. The method of claim 1, wherein the mushroom is selected from a species occurring in *Amanita, Agaricus, Boletus, Lactarius, Lepiota, Russula, Tricholoma, Coprinus*, or *Pluteus* genus.

4. The method of claim 1, wherein the first solvent system comprising water and a polar organic solvent.

5. The method of claim 4, wherein the polar organic solvent comprises an alcohol selected from methanol, ethanol, propanol, or a mixture thereof.

6. The method of claim 5, wherein the aqueous solvent system comprises water and methanol present in a volume ratio of from 1:5 to 5:1.

7. The method of claim 1, wherein the second solvent system comprises a polar organic solvent, a non-polar organic solvent, or a mixture thereof.

8. The method of claim 1, wherein the second solvent system consists essentially of an alcohol.

9. The method of claim 1, wherein step b) and step c) are carried out at a temperature from 80° C. to 160° C.

10. The method of claim 1, having a yield of at least 80% by weight cyclopeptide toxins, based on the total amount of cyclopeptide toxins from the mushroom.

11. A method for extracting cyclopeptide toxins from a mushroom comprising:
    a) mixing a sample of the mushroom with sand;
    b) contacting the sample with a first solvent system in an extraction cell at a temperature of 80° C. or greater for a sufficient time to extract at least a first portion of cyclopeptide toxins from the sample; and
    c) contacting the sample with a second solvent system in an extraction cell at a temperature of 80° C. or greater for a sufficient time to extract at least a second portion of cyclopeptide toxins from the sample.

12. The method of claim 11, wherein the biological sample is obtained from a mushroom.

* * * * *